(12) United States Patent
Kopelman et al.

(10) Patent No.: US 8,301,287 B2
(45) Date of Patent: *Oct. 30, 2012

(54) METHOD AND SYSTEM FOR FABRICATING A DENTAL COPING, AND A COPING FABRICATED THEREBY

(75) Inventors: Avi Kopelman, Palo Alto, CA (US); Eldad Taub, Reut (IL)

(73) Assignee: Cadent Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/189,398

(22) Filed: Jul. 22, 2011

(65) Prior Publication Data

US 2011/0282474 A1 Nov. 17, 2011

Related U.S. Application Data

(63) Continuation of application No. 12/149,102, filed on Apr. 25, 2008, now Pat. No. 7,996,099, which is a continuation of application No. 11/498,791, filed on Aug. 4, 2006, now Pat. No. 7,383,094, which is a continuation of application No. 11/214,882, filed on Aug. 31, 2005, now Pat. No. 7,110,844, which is a continuation of application No. 10/814,653, filed on Apr. 1, 2004, now Pat. No. 6,957,118.

(60) Provisional application No. 60/459,624, filed on Apr. 3, 2003.

(51) Int. Cl.
*G06F 19/00* (2011.01)
*A61C 11/00* (2006.01)

(52) U.S. Cl. .......................... 700/98; 700/118; 433/223

(58) Field of Classification Search .................... 700/98, 700/118, 163; 433/218, 233
See application file for complete search history.

(56) References Cited

U.S. PATENT DOCUMENTS

4,324,546 A * 4/1982 Heitlinger et al. .............. 433/25
* cited by examiner

*Primary Examiner* — Ryan Jarrett
(74) *Attorney, Agent, or Firm* — Wilson Sonsini Goodrich & Rosati (57) ABSTRACT

A wax model of a required coping is produced using CNC machining techniques based on a virtual model of the coping created from digital data obtained from the intraoral cavity. The dental coping is then fabricated from the wax model.

34 Claims, 4 Drawing Sheets

METHOD AND SYSTEM FOR FABRICATING A DENTAL COPING, AND A COPING FABRICATED THEREBY

CROSS-REFERENCES TO RELATED APPLICATIONS

This application is a Continuation of U.S. Application Ser. No. 12/149,102, which is a Continuation of U.S. Application Ser. No. 11/498,791, filed on Aug. 4, 2006 (now U.S. Pat. No. 7,383,094, issued on Jun. 3, 2008), which is a Continuation of U.S. Application Ser. No. 11/214,882, filed on Aug. 31, 2005 (now U.S. Pat. No. 7,110,844, issued on Sep. 19, 2006), which is a Continuation of U.S. Application Ser. No. 10/814,653, filed on Apr. 1, 2004 (now U.S. Pat. No. 6,957,118, issued on Oct. 18, 2005), claiming the benefit under 35 USC 119(e) of U.S. Provisional Application No. 60/459,624, filed on Apr. 3, 2003, the entire contents of each of which is hereby incorporated herein by reference in its entirety.

FIELD OF THE INVENTION

This invention relates to teeth restoration, specifically to a method and system for fabricating dental copings for crowns and/or bridges, and to the copings made thereby.

BACKGROUND OF THE INVENTION

In the field of teeth restoration, metal copings are typically used in the construction of a dental crown and/or bridge. The metal coping functions as the understructure of the crown, and is typically covered with a coating of ceramic porcelain composition or a polymer-based veneering material. The metal coping supports the coating and provides the required structural strength and rigidity for the restored tooth to resist the forces of mastication.

There are methods in the art for the production of metal coping by casting it from a wax pattern, for example by the known "lost wax" technique. An accurate working model of the patient's teeth, which includes the preparation (die) of the tooth (or teeth) to be restored and its surrounding area, is used. As discussed in Kuwata et al., Color Atlas of Ceramo-Metal Technology (Ishiyaku EuroAmerica, Inc., 1986, pp. 96-101), a wax coping, which is an exact replication of the desired metal coping, is manually built by wrapping a thin sheet of wax around the working model of the preparation, and is adapted to the preparation surface. By using a heated carving knife, the margin of the adapted sheet wax is cut off and the sheet joints are bent and sealed by adding more wax. The wax margin is further processed in order to correspond to the margin line of the restoration, i.e. by additional carving and/or wax adding.

The finished wax-up of the coping is then removed from the working model and invested in a material that solidifies onto the external side of the wax coping and forms a mold (this stage is known as the "investment" stage). The combined structure is then heated such that the wax is burnt out, leaving a cavity into which the metal is cast. After hardening, the mold is removed from the metal casting.

Another method for producing metal coping involves a direct fabrication of the metal coping based on digital data. U.S. 2002/0137011 discloses an automated and digital method for the formation of the metal coping from a sheet of metallic material, which comprises: scanning a three dimensional image of the die of the tooth or teeth to be restored; digitizing the scanned three dimensional image into digital information, storing the digital information in a computer; feeding the digital information from the computer into a CNC (computerized numerical control) cutting machine; cutting out a section of material of metallic composition into a two dimensional configuration representing a two dimensional lay out of the scanned three dimensional image, adapting the cut out section of material over the die so that the material covers the die surface in close engagement therewith to form a single three dimensional structure having the shape of the die and heat treating the structure, into a coping, conforming in shape to the die.

WO 03/017864 discloses a method for producing a dental prosthesis such as a dental coping. The method comprises the following steps: obtaining three-dimensional digital data relating to a patient's dentition; designing a virtual prosthesis for the dentition using the three-dimensional digital data; transmitting digital data corresponding to the virtual prosthesis to an automated prototyping system; producing a prototype of the dental prosthesis with the automated prototyping system, the prototype made of a material that can be ablated; covering at least the prototype with a hardening material and removing the prototype from within said hardening material to produce a mold for the dental prosthesis; casting the dental prosthesis by filling the mold with a metal and removing the hardening material.

In the case of coping fabrication in the "lost wax" technique, be it the manual production or the automated, prototype production, the wax is used as it is easy to manipulate and allows a high level of accuracy. Typically, soft wax, i.e. wax with relatively high viscosity, is used. Special care must be taken in handling the soft wax, as it is very sensitive to physical stress. Indeed, any damage to the wax-up pattern before investment (i.e. during its production process or after) may lower the quality of the replicated dental coping.

Of general background interest, the following patents describe manufacturing methods for prostheses. In U.S. Pat. No. 4,663,720 and U.S. Pat. No. 4,742,464 an apparatus and method are disclosed for designing a prosthesis starting with a 3D model of the patient's dentition obtained by optical methods, and directly machining the prosthesis from a blank. In U.S. Pat. No. 5,092,022, a prosthesis or a negative mold therefor can be machined automatically from suitable materials, with the assistance of a computer which takes into consideration, inter alia, the shape of the zone of implantation previously obtained. In U.S. Pat. No. 5,452,219, a negative mold for a prosthesis is milled using a machine controlled by a program based on 3D data obtained from a tooth model. In U.S. Pat. No. 5,378,154 a method for machining a dental prosthesis is disclosed, wherein the outside visible part of the prosthesis is subjected to a material removal operation by means of a CNC machining tool which follow machining paths that follow 3D irregularly spaced curved lines. In U.S. Pat. No. 6,126,732, a shaped high-strength dental ceramic prosthesis is made by pressing a molding composition comprising 1-50 wt % glass particles and about 50-99 wt % ceramic particles to form a ceramic frame, veneering the frame and firing the coated frame. In U.S. Pat. No. 5,691,905 and U.S. Pat. No. 5,718,585 methods of milling and polishing a set of negative mold parts are disclosed. In U.S. Pat. No. 6,488,503, a process is described for producing an artificial tooth, in which polymerizable materials are injection molded into a mold in stages to produce a solid core applied on an inner layer, which is applied on an external layer of the artificial tooth. In U.S. Pat. No. 6,066,274, a device including an injection molding tool is disclosed for producing a sinterable ceramic and/or metallic product using engageable molding tool parts one of which is produced using a wet composition. In U.S. Pat. No. 5,382,164, a method of making restorations is disclosed, comprising: temporarily repairing a tooth area to be restored to a final shape, and taking a first impression of the tooth area to be restored; preparing the tooth to be restored, and taking a second impression within the first impression to form a physical model of the crown. This model is then scanned to provide an image thereof, and a computer uses this image to mill the final restoration.

SUMMARY OF THE INVENTION

The present invention provides, in its first aspect, a method and system for fabricating a dental coping for dental prosthesis of at least one tooth which is to be fitted over a tooth preparation. The method comprises providing three-dimensional (3D) digital data relating to the patient's dentition, which includes data representative of the surface topology of the preparation and its surroundings. The method further comprises generating a three-dimensional (3D) virtual model of a dental coping for the tooth, such that the inner surface of the virtual coping fits over a portion of the surface of the tooth preparation in close engagement. Alternatively, a virtual model of the final required restoration may be created, and the internal surface of the required coping is derived from this model; a suitable external surface for the coping can be designed in any suitable manner. The method further comprises generating a computerized numerical control (CNC) set of instructions corresponding to the 3D model of said coping. Based on said set of instructions, a model coping is fabricated from wax or other low fusion temperature material, by a computerized numerical control (CNC) milling machine. From the fabricated coping wax model, a dental coping is fabricated. The system comprises means for providing three-dimensional (3D) digital data relating to the patient's dentition, which includes data representative of the surface topology of the preparation and its surroundings. The system further comprises means for generating a three-dimensional (3D) virtual model of a dental coping for the tooth, such that the inner surface of the virtual coping fits over a portion of the surface of the tooth preparation in close engagement. The system further comprises means for generating a computerized numerical control (CNC) set of instructions corresponding to the 3D model of said coping. The system also comprises means for fabricating a model of the coping from wax or other low fusion temperature material, by a computerized numerical control (CNC) milling machine, based on said set of instructions. The system further comprises means for fabricating a dental coping from the fabricated coping wax model.

The present invention also provides a method and system for the fabrication of a coping wax model that is to be used for fabricating a dental coping for a dental prosthesis of at least one tooth that is to be fitted over a tooth preparation. This method comprises providing three-dimensional (3D) digital data relating to the patient's dentition, which includes data representative of the surface topology of the tooth preparation and its surroundings; generating a three-dimensional (3D) virtual model of a dental coping for the tooth, such that the inner surface of the virtual coping fits over a portion of the surface of the tooth preparation in close engagement; generating a computerized numerical control (CNC) set of instructions corresponding to the 3D model of said coping; and based on said set of instructions, fabricating a wax coping by a computerized numerical control (CNC) milling machine. The system comprises means for providing three-dimensional (3D) digital data relating to the patient's dentition, which includes data representative of the surface topology of the tooth preparation and its surroundings; means for generating a three-dimensional (3D) virtual model of a dental coping for the tooth, such that the inner surface of the virtual coping fits over a portion of the surface of the tooth preparation in close engagement; means for generating a computerized numerical control (CNC) set of instructions corresponding to the 3D model of said coping; and based on said set of instructions, means for fabricating a wax coping by a computerized numerical control (CNC) milling machine.

The term "tooth preparation" as used herein refers both to one or more tooth stumps or pivots (also known as cores or posts) prepared by the care provider on the basis of an original tooth or an implant which serves as a basis for the dental prosthesis (e.g. crown or bridge).

The term "dental coping" as used herein refers to a support structure for a crown, i.e. structure that cups only one tooth, as well as a support structure for a bridge, i.e. structure that cups more than one tooth. The term "dental coping" as used herein, also refers to the cup, which may be made from metals or ceramics, for example, and all other prosthesis elements such as connectors and pontics, as the case may be. The dental coping may be fabricated from suitable materials such as metal, ceramo-metal materials, etc.

The 3D digital data may be obtained by a number of ways known per se. For example, such digital data may be obtained in a manner as described in WO 00/08415, U.S. Patent Application No. 2002/0137011 or in any of U.S. Pat. Nos. 6,099,314 and 6,334,853, or any combination thereof. The 3D data includes the surface topology of the preparation, as well as its surroundings. Furthermore, such 3D) digital data may also comprise other data, for example, data that was added by the orthodontist or a dental technician, such as the preparation's finish line.

The 3D virtual model of the dental coping may be produced in a number of ways. By one example, the dentist, orthodontist, etc. (to be referred to herein collectively as the "care provider") designs the overall outer surface of the tooth prosthesis and then, based on known considerations of enamel thickness as well as coping thickness, the coping is designed so as to fit below the surface of the tooth prosthesis and over the tooth preparation. As known per se, some room needs to be reserved for adhesive materials.

By another example, the coping is designed primarily on the basis of the surface topology of the preparation and other factors such as the coping wall's thickness, finish line data, etc.

The generation of the virtual 3D coping data may be automatic, manual or a combination thereof.

The term "wax" includes any material that is relatively hard and lends itself to machining, particularly milling, while having a sufficient low melting point and appropriate kinematic viscosity that renders it suitable for use in a lost wax process or the like.

The wax that should be used in accordance with the invention is hard and durable that lends itself to milling in a milling machine. Another requirement of the wax is that after melting, it should have a viscosity sufficiently low to be usable in a lost wax technique known per se in the art of metal casting.

A typical wax that can be used in accordance with the invention is such having a melting point and congealing point of 55-80° C. and a kinematic viscosity of less than 90 m$^2$sec. at about 100° C.

As will be appreciated, the coping prepared in accordance with the invention may be suitable for a single tooth, (in the case of a single tooth prosthesis), or a coping that serves as a basis for a bridge.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1A:
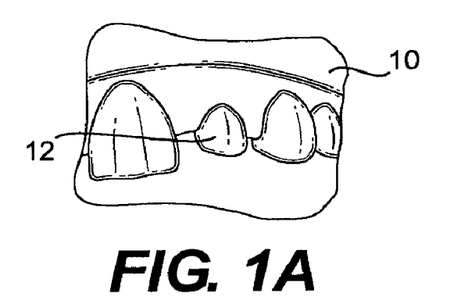
FIGS. 1A-1E illustrate an exemplary scenario for the fabrication of a dental coping in which the invention is implemented.

FIGS. 1A-1E illustrate an exemplary scenario for the fabrication of a dental coping in which the invention is implemented. The scenario is carried out with the aid of a computer system, the operation of which will be explained later on. FIG. 1A shows a section 10 of a patient's teeth (part of the patient's upper jaw, in this example), in which tooth prosthesis is to be fitted over tooth preparation 12. In the example of FIG. 1A, the root and base of the tooth 12 are sufficiently strong and healthy, and the care provider prepared the tooth for the crown by removing a portion of the enamel and dentin. If the tooth to be restored is severely decayed or weak, then it may be necessary to insert a metal implant or pivot (also known as cores or posts) by any one of a number of ways known per se.

Figure 3:
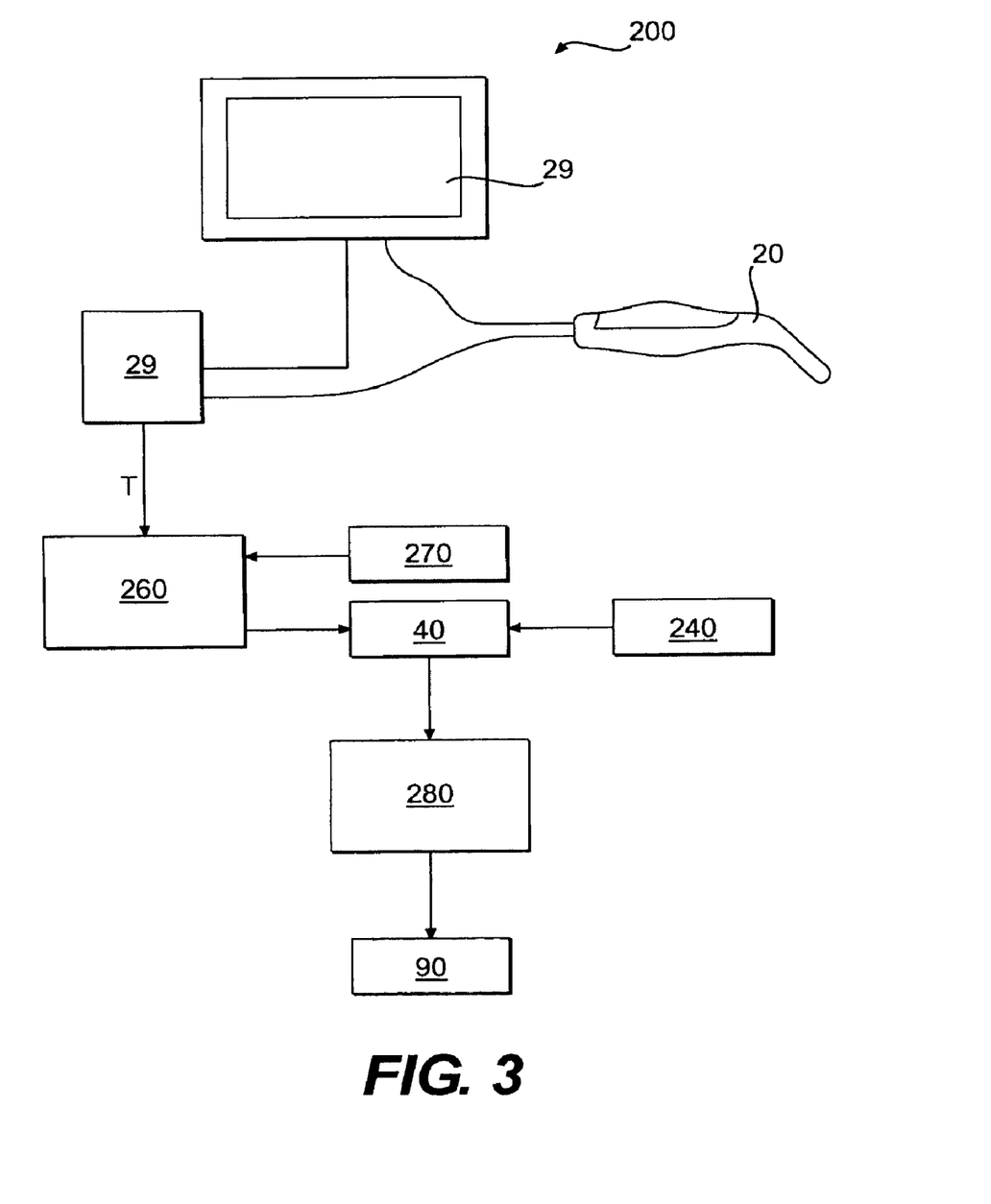
FIG. 3 shows a block diagram of fabrication system according to the invention.

An exemplary system 300 for carrying out the process of the invention is illustrated in FIG. 3.

The 3D digitized data of the intraoral cavity, including the dentition and associated anatomical structures of a patient is obtained, and thus suitable equipment for scanning a patient's teeth is used by the care provider to acquire the 3D data. The production of the virtual 3D working model of the preparation and its surroundings is known per-se.

Figure 1B:
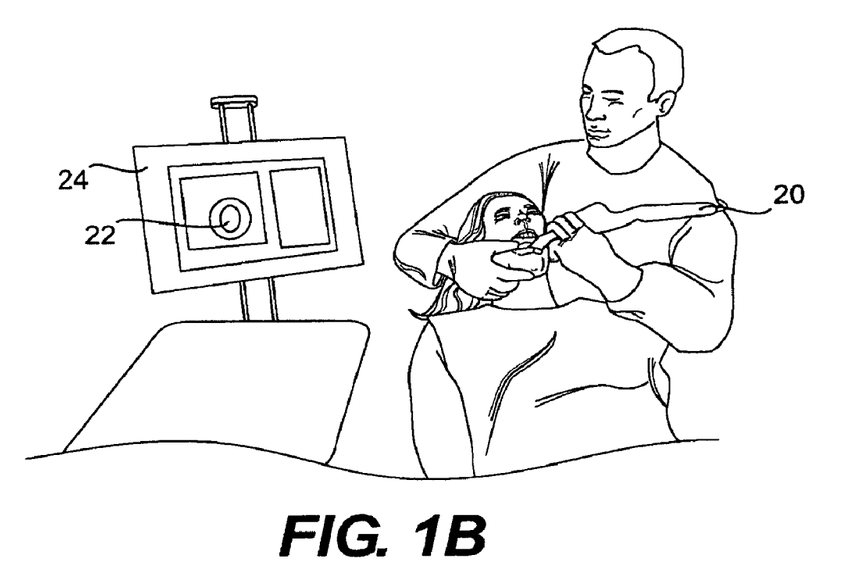

As shown in FIG. 1B, for example, the care provider captures an image of the preparation and its surroundings with a probing device 20. Advantageously, a probe for determining three dimensional structure by confocal focusing of an array of light beams may be used, for example as manufactured under the name of PROSTHOCAD or as disclosed in WO 00/08415, the contents of which are incorporated herein in their entirety. Alternatively, scanning of the dental cavity to provide the 3D data may be accomplished using a suitable apparatus, for example as disclosed in any one of U.S. Pat. Nos. 4,837,732, 4,611,288, 6,594,539, 6,402,707, and 6,364,660, US 2002/0028418, US 2002/0058229, U.S. Pat. Nos. 5,652,709, 4,575,805, 5,733,126, 5,880,962, 4,742,464, and 4,663,720, WO 02/071306 mutatis mutandis. The contents of these publications are incorporated herein in their entirety by reference thereto.

The 3D data obtained by the probe may then be stored in a suitable storage medium, for example a memory in a computer workstation, for further processing, as described herein.

Alternatively, a negative cast or impression is taken of the patient's teeth, in a manner known in the art, and this negative model and a positive cast is made from this model suitable for scanning. The positive cast may be scanned by any method known in the art, including using the aforesaid probe manufactured under the name of PROSTHOCAD or as disclosed in WO 00/08415. Alternatively, the negative model itself may be scanned.

Alternatively, a composite positive-negative model may be manufactured from the original negative model. Thereafter, the positive-negative model may be processed to obtain 3D digitized data, for example as disclosed in U.S. Pat. No. 6,099,314, assigned to the present assignee, and the contents of which are incorporated herein in their entirety.

Alternatively, the 3D digitized data may be obtained in any other suitable manner, including other suitable intra oral scanning techniques, based on optical methods, direct contact methods or any other means, applied directly to the patient's dentition. Alternatively, X-ray based, CT based, MRI based, or any other type of scanning of the patient or of a positive and/or negative model of the intra-oral cavity may be used. The digitized data may be associated with a complete dentition, or of a partial dentition, for example such as a preparation only of the intra oral cavity.

Referring to FIG. 3, a virtual 3D working model 22 is digitally produced by a processor, 29 and may well be displayed on display 24.

Figure 1C:
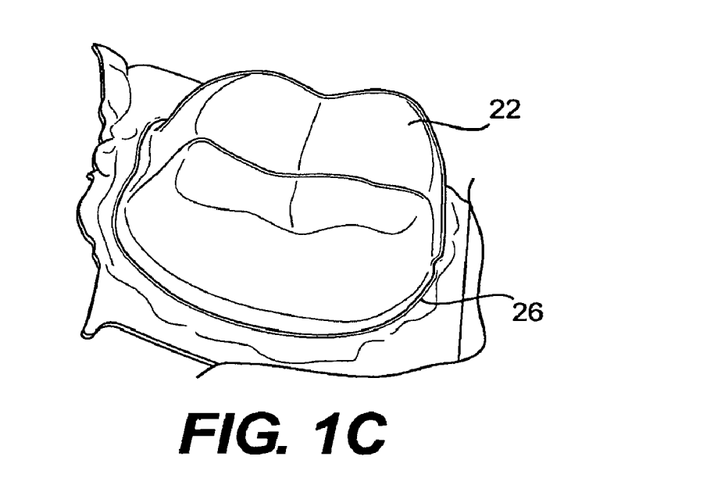
Figure 1D:
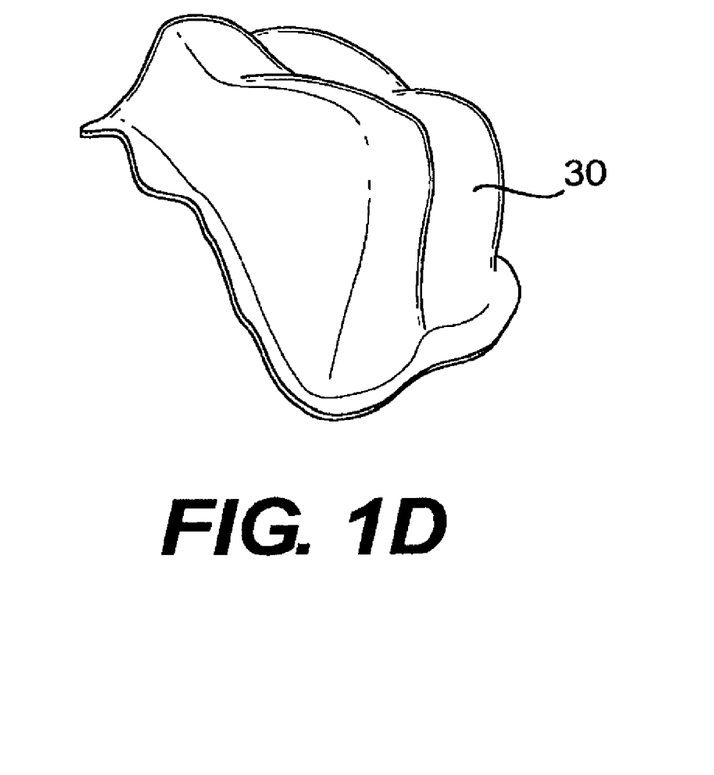
Figure 1E:
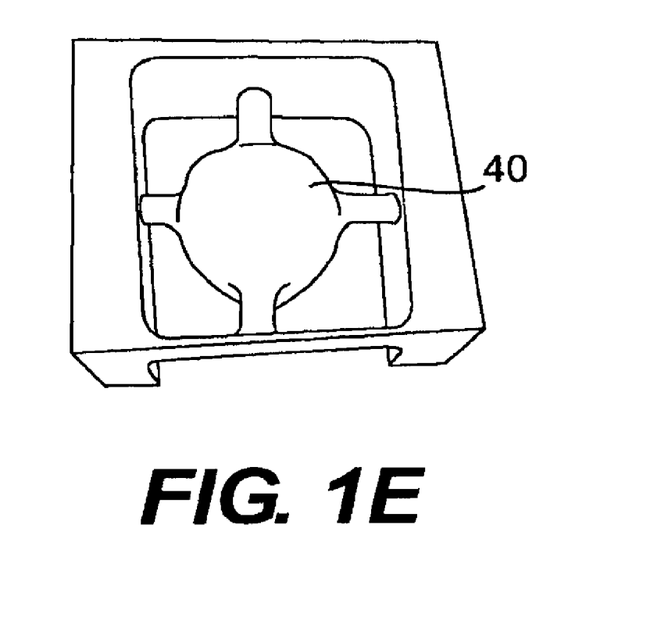

FIG. 1C shows the virtual working model 22 in a magnified manner, with its finish line 26 (also known as the margin line) that was either generated automatically or marked by the care provider. The virtual model 22 and the finish line 26 data, and perhaps additional 3D data that relates to the patient's dentition, are processed and then input to a CAD (Computer-Aided Design) unit (not shown) that allows for the digital design of the dental coping, resulting in the virtual coping 30, shown in FIG. 1D.

The virtual coping 30 may then be further processed by a CAM (Computer-Aided Manufacture) unit (not shown) to generate a digital set of instructions T that are fed into a CNC (computerized numerical control) milling machine 260, from which a wax coping 40 (as the one shown in FIG. 1E) is milled using wax or the like supplied from supply 270. Wax coping 40 is made of relatively hard, durable wax or similar material. In particular, the coping 40 is made from a material that on the one hand lends itself to milling in a milling machine, while on the other hand has a low melting point and after melting, it has a kinematic viscosity sufficiently low to be usable in a lost wax technique known per se in the art of metal casting. Preferably, such a material has a melting point and congealing point of about 55° C. to about 80° C. and a kinematic viscosity of less than 90 m$^2$sec. at about 100° C.

The desired dental coping 90 is then produced from the wax coping, according to common dental practice, via suitable manufacturing means 280.

The finish line data can be generated for example, in a manner disclosed in U.S. Ser. No. 10/623,707 and WO 04/008981 also assigned to the present assignee, and the contents of which are incorporated herein in their entirety. Alternatively, the finish line may be generated using methods disclosed in U.S. Pat. No. 5,266,030 the contents of which are incorporated herein. The virtual generation of the finish line may be incorporated as an integral component in the method of the invention.

The additional 3D data that relates to the patient's dentition includes, inter-alia, information relating to the surrounding of the tooth to be restored, e.g. 3D representation of the patient's dentition, including the upper and lower jaws and their occlusion relationship. Such information is needed, e.g. for the design of the dental crown, and can be generated for example, as disclosed in U.S. Pat. No. 6,099,314 and U.S. Pat. No. 6,334,853.

The virtual model of the desired coping can be generated in several ways. According to one possible way, the care provider designs the overall outer surface of the tooth prosthesis, based on known considerations such as enamel thickness, as well as coping thickness and others. The coping is designed so as to fit below the surface of the tooth prosthesis and over the tooth preparation. By another example, the coping is designed primarily on the basis of the surface topology of the preparation and other factors such as the coping wall's thickness, finish line data, etc.

In particular, the external surface of the coping, which eventually mates with a cap or the like which may be single-layered or multi-layered, is designed according to predetermined criteria, as known in the art, to provide the required mechanical properties required from the restoration.

The virtual coping 30 may also be created in other ways. For example, a physical model of the restoration may be created in any suitable manner, for example as disclosed in U.S. Pat. No. 5,382,164, the contents of which are incorporated herein in their entirety. The inner surface of such a model, preferably including the finish line, may be scanned in any suitable manner, similar, for example to that described above for the preparation, mutatis mutandis, Alternatively, a virtual model of the full restoration may be used to provide the internal surface and preferably the finish line for the coping. Then, an external surface for the coping may be designed according to any suitable criteria, for example as described above, and the virtual model corresponding to the external surface may be joined to the virtual model of the inner surface to provide the virtual coping 30.

The method of the present invention in fact makes use of the "lost wax" technique, by utilizing relatively hard, durable wax, which can be milled to the desired pattern by a CNC milling machine.

Figure 2:
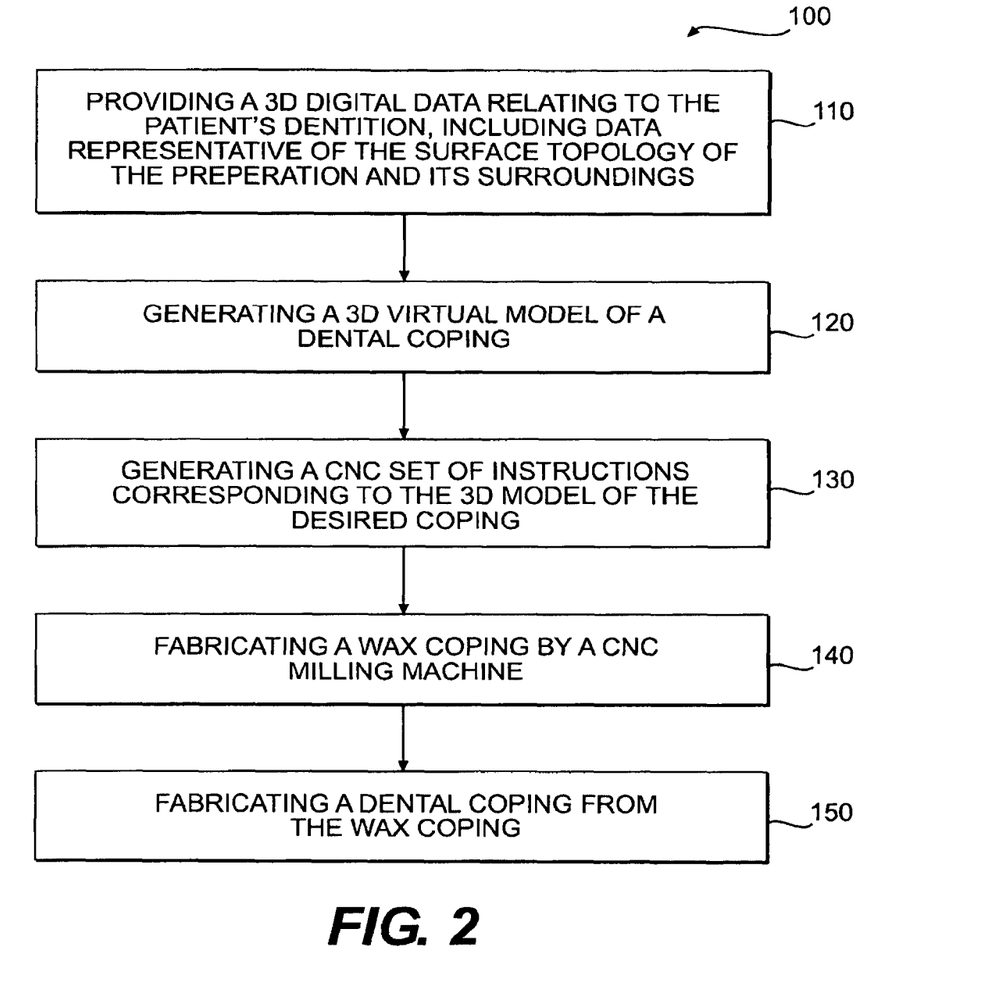
FIG. 2 shows a block diagram of fabrication processes according to the invention.

FIG. 2 shows a block diagram of fabrication processes 100 according to the invention. At step 110, a three-dimensional (3D) digital data is provided. The 3D digital data relates to the patient's dentition, including data representative of the surface topology of the preparation and its surroundings. At step 120, a 3D virtual model of a dental coping is generated.

At step 130, a CNC (Computerized Numerical Control) set of instructions corresponding to the 3D virtual model of the desired coping is generated, and fed into a CNC milling machine for the fabrication of a wax coping (step 140), wherein a wax coping is produced from a suitable block of wax or the like.

Optionally, and particularly when the final prosthesis is a bridge, wax replicas of suitable connectors and/or one or more pontics are made, either manually or by any suitable method, including machining, casting and so on, indicated at 240 in FIG. 3. Then, the connectors and/or pontics are joined to the wax copings of the abutment teeth in a suitable manner, for example as is known in the art per se. The metal or ceramic structure for the bridge is then made from the wax model thereof in a similar manner to that described below for a single coping, mutatis mutandis.

At step 150, the dental coping is fabricated from the wax coping. This may be accomplished in any number of ways, known per se in the art. For example, the wax coping is invested in a material that solidifies onto the external side of the wax coping and forms a mold. After the investment stage, the combined structure is then heated such that the wax is burnt out, leaving a cavity. Into this cavity, a suitable molten metal may be injected, and after hardening, the mold is removed from the metal casting to provide a metal coping. Such a lost wax process may be similar to the process used for the production of restorations as described by Ivoclar Vivadent Ltd. regarding the IPS Empress system in http://www.ivoclar.co.uk/technician/nonmetal2.html, mutatis mutandis, for example Alternatively, a suitable ceramic molding composition may be pressed into the cavity, for example as described in U.S. Pat. No. 6,126,732, mutatis mutandis, the contents of which are incorporated herein in their entirety. Alternatively, sintering methods may be applied to the mold to produce a ceramic coping.

Alternatively, the wax coping may be scanned and the coping produced in a manner similar to the production of crowns and bridges, as described by DeguDent regarding the Cercon system in http://www.degudent.com/Products/Cercon_smart_ceramics/index.asp, mutatis mutandis.

The dental coping manufactured according to the present invention is thus derived from a wax model, which due to its relatively softness can be machined to a smoother surface texture than is possible when machining the coping directly from the desired final material such as metal or a ceramic. Accordingly, dental copings produced using the method of the invention using the wax for preparing a mold are correspondingly smoother, and furthermore it is possible to include fine details in the final coping, with respect to copings produced using direct material removal methods applied to the final material.

Furthermore, the wax-based method of the present invention for producing the dental coping has some advantages over direct material removal methods that are used elsewhere for producing the coping directly from the desired final material. For example less wear and breakage are experienced by the machining tool, and thus lowers costs. Furthermore, deformations of the tool, when a direct contact tool such as for example a mechanical tool is used, is less likely, and thus less deviations from the nominal dimensions of the coping with respect to the virtual model thereof occur than when producing a coping directly from a metal or other hard material.

The invention allows to gather the 3D data that represents the patient's dentition in one place (say, the care provider's clinic), to design the virtual coping model at the clinic or at a remote location, to generate the CNC set of instructions at another place and to fabricate the wax coping at a yet another location. Furthermore, the invention allows for the fabrication of the wax coping and the dental coping at different locations without damaging the quality of the dental coping due to deformations in the coping wax model. It should be noted that additional, intermediate steps in which digital data is transmitted between remote locations might be carried-out as part of method 100, for example between steps 110 and 120, etc.

The invention is not bound by the specified example of FIGS. 1A-1E and, accordingly, other scenarios may be used in addition or in lieu of the above, depending upon the particular application. Specifically, the invention can also be utilized in a less "digitized" scenario, for example one in which the care provider gathers the relevant information relating to the patient's dentition in a non-digitized manner (e.g. by taking a physical impression of the patient's dentition), and the patient's dentition data is digitized later on, at a laboratory.

Furthermore, the invention can be utilized for the fabrication of the dental prostheses as a whole, as needed, for example, when restoring the tooth with a gold prosthesis. In that case, a wax model of the desired prosthesis is fabricated, from which a whole metal prosthesis is replicated.

The invention claimed is:

1. A method for the manufacture of at least a prosthesis portion of a dental prosthesis of at least one tooth to be fitted over a tooth preparation, comprising:
   fabricating a wax model of the prosthesis portion, wherein at least a first, inner surface of said wax model is manufactured by computerized numerical control (CNC) milling of the model according to suitable CNC instructions, wherein said CNC instructions are based on a three-dimensional (3D) virtual model of the prosthesis portion that is virtually generated based on processing of 3D digital data of at least said tooth preparation, and further comprising the step of manufacturing the prosthesis portion from the wax model.

2. A method according to claim 1, wherein said CNC instructions are generated according to the steps:
   a) providing said three-dimensional (3D) digital data relating to the patient's dentition, said 3D data including data representative of the surface topology of said preparation and its surroundings;
   b) generating said three-dimensional (3D) virtual model of at least a portion of said at least one tooth based on said 3D digital data corresponding to said prosthesis portion; and
   c) generating said CNC instructions corresponding to at least a part of the 3D virtual model of said portion corresponding to said inner surface of said 3D virtual model.

3. A method according to claim 2, wherein in step (c), further CNC instructions are generated corresponding to a second surface of said virtual model, wherein said second surface is an outer surface with respect to said first surface, and wherein a second surface of said wax model corresponding to said second surface of said 3D virtual model is manufactured by computerized numerical control (CNC) milling of the model according to said further CNC instructions.

4. A method according to claim 2, wherein step (a) is performed according to at least one of: using suitable optical scanner; and directly on the intraoral cavity comprising said preparation.

5. A method according to claim 2, wherein said digital data of step (a) is obtained from a virtual model of the prosthesis, wherein the prosthesis is designed for said preparation.

6. A method according to claim 1, wherein the step of manufacturing the prosthesis portion from the wax model comprises a lost wax process.

7. A method according to claim 1, wherein said prosthesis portion is made from any one of a suitable metal and a suitable ceramic material.

8. A method according to claim 1, wherein said prosthesis portion is adapted for being a part of any one of a crown prosthesis and a bridge prosthesis.

9. A method according to claim 1, wherein said prosthesis portion is adapted for being a part of a bridge prosthesis, and further comprises the steps of providing wax replicas of suitable connectors and/or one or more pontics, and joining said replicas to wax models of the copings required for said prosthesis.

10. A prosthesis portion, fabricated according to the method of claim 1.

11. A method for the manufacture of a prosthesis part wax model to be used in the manufacture of a prosthesis portion of a dental prosthesis of at least one tooth to be fitted over a tooth preparation, comprising fabricating a wax model of the prosthesis portion, wherein at least a first, inner surface of said wax model is manufactured by computerized numerical control (CNC) milling of the model according to suitable CNC instructions, wherein said CNC instructions are based on a three-dimensional (3D) virtual model of the prosthesis portion that is virtually generated based on processing of 3D digital data of at least said tooth preparation.

12. A method according to claim 11, wherein said CNC instructions are generated according to the steps:
   a) providing said three-dimensional (3D) digital data relating to the patient's dentition, said 3D data including data representative of the surface topology of said preparation and its surroundings;
   b) generating said three-dimensional (3D) virtual model of at least a portion of said at least one tooth based on said 3D digital data corresponding to said prosthesis portion; and
   c) generating said CNC instructions corresponding to at least a part of the 3D virtual model of said portion corresponding to said inner surface of said 3D virtual model.

13. A method according to claim 12, wherein in step (c), further CNC instructions are generated corresponding to a second surface of said virtual model, wherein said second surface is an outer surface with respect to said first surface, and wherein a second surface of said wax model corresponding to said second surface of said 3D virtual model is manufactured by computerized numerical control (CNC) milling of the model according to said further CNC instructions.

14. A method according to claim 12, wherein step (a) is performed according to at least one of: using a suitable optical scanner; and directly on the intraoral cavity comprising said preparation.

15. A method according to claim 12, wherein said digital data of step (a) is obtained from a virtual model of a prosthesis designed for said preparation.

16. A method according to claim 11, wherein said wax model is adapted for the manufacture of any one of a crown prosthesis and a bridge prosthesis.

17. A method according to claim 11, wherein said wax model is adapted for the manufacture of a bridge prosthesis, and further comprises the steps of providing wax replicas of suitable connectors and/or one or more pontics, and joining said replicas to wax models of the copings required for said prosthesis.

18. A wax model, fabricated according to the method of claim 11.

19. A system for the manufacture of at least a prosthesis portion of a dental prosthesis of at least one tooth to be fitted over a tooth preparation, the system comprising:
   a processor;
   a computerized numerical control (CNC) milling machine; and
   manufacturing means,
   wherein the system is configured for fabricating a wax model of the prosthesis portion, wherein at least a first, inner surface of said wax model is manufactured by computerized numerical control (CNC) milling of the model according to suitable CNC instructions, wherein said CNC instructions are based on a three-dimensional (3D) virtual model of the prosthesis portion that is virtually generated based on processing of 3D digital data of at least said tooth preparation,
   wherein the system is further configured for manufacturing the prosthesis portion from the wax model.

20. A system according to claim 19, wherein the system is configured for generating said CNC instructions according to the steps:
   a) providing said three-dimensional (3D) digital data relating to the patient's dentition, said 3D data including data representative of the surface topology of said preparation and its surroundings;
   b) generating said three-dimensional (3D) virtual model of at least a portion of said at least one tooth based on said 3D digital data corresponding to said prosthesis portion; and c) generating said CNC instructions corresponding to at least a part of the 3D virtual model of said portion corresponding to said inner surface of said 3D virtual model.

21. A system according to claim 20, wherein in step (c), further CNC instructions are generated corresponding to a second surface of said virtual model, wherein said second surface is an outer surface with respect to said first surface, and wherein a second surface of said wax model corresponding to said second surface of said 3D virtual model is manufactured by computerized numerical control (CNC) milling of the model according to said further CNC instructions.

22. A system according to claim 20, wherein the system comprises a suitable optical scanner for executing step (b).

23. A system according to claim 20, wherein said digital data of step (a) is obtained from a virtual model of the prosthesis, wherein the prosthesis is designed for said preparation.

24. A system according to claim 19, wherein system is configured for manufacturing the prosthesis portion from the wax model via a lost wax process.

25. A system according to claim 19, wherein said prosthesis portion is made from any one of a suitable metal and a suitable ceramic material.

26. A system according to claim 19, wherein said prosthesis portion is adapted for being a part of any one of a crown prosthesis and a bridge prosthesis.

27. A system according to claim 19, wherein said prosthesis portion is adapted for being a part of a bridge prosthesis, and further comprises the steps of providing wax replicas of suitable connectors and/or one or more pontics, and joining said replicas to wax models of the copings required for said prosthesis.

28. A system for the manufacture of a prosthesis part wax model to be used in the manufacture of a prosthesis portion of a dental prosthesis of at least one tooth to be fitted over a tooth preparation, the system comprising:
   a processor, and
   a computerized numerical control (CNC) milling machine, wherein the system is configured for fabricating a wax model of the prosthesis portion, wherein at least a first, inner surface of said wax model is manufactured by computerized numerical control (CNC) milling of the model according to suitable CNC instructions, wherein said CNC instructions are based on a three-dimensional (3D) virtual model of the prosthesis portion that is virtually generated based on processing of 3D digital data of at least said tooth preparation.

29. A system according to claim 28, wherein the system is configured for generating said CNC instructions according to the steps:
   (a) providing said three-dimensional (3D) digital data relating to the patient's dentition, said 3D data including data representative of the surface topology of said preparation and its surroundings;
   (b) generating said three-dimensional (3D) virtual model of at least a portion of said at least one tooth based on said 3D digital data corresponding to said prosthesis portion;
   (c) generating said CNC instructions corresponding to at least a part of the 3D virtual model of said portion corresponding to said inner surface of said 3D virtual model.

30. A system according to claim 29, wherein in step (c), further CNC instructions are generated corresponding to a second surface of said virtual model, wherein said second surface is an outer surface with respect to said first surface, and wherein a second surface of said wax model corresponding to said second surface of said 3D virtual model is manufactured by computerized numerical control (CNC) milling of the model according to said further CNC instructions.

31. A system according to claim 29, wherein the system comprises a suitable optical scanner for executing step (b).

32. A system according to claim 29, wherein said digital data of step (a) is obtained from a virtual model of a prosthesis designed for said preparation.

33. A system according to claim 28, wherein said wax model is adapted for the manufacture of any one of a crown prosthesis and a bridge prosthesis.

34. A system according to claim 28, wherein said wax model is adapted for the manufacture of a bridge prosthesis, and further comprises the steps of providing wax replicas of suitable connectors and/or one or more pontics, and joining said replicas to wax models of the copings required for said prosthesis.

* * * * *